United States Patent
Sunagawa et al.

(10) Patent No.: US 6,599,895 B1
(45) Date of Patent: Jul. 29, 2003

(54) β-LACTAM COMPOUNDS AND PROCESS FOR PRODUCING THE SAME

(75) Inventors: Makoto Sunagawa, Itami (JP); Hiroshi Yamaga, Suita (JP); Yoshihiro Sumita, Nara-ken (JP); Hisatoshi Shinagawa, Takatsuki (JP)

(73) Assignee: Sumitomo Pharmaceuticals Company, Limited, Osaka-fu (JP)

( * ) Notice: Subject to any disclaimer, the term of this patent is extended or adjusted under 35 U.S.C. 154(b) by 0 days.

(21) Appl. No.: 09/674,430

(22) PCT Filed: Apr. 28, 1999

(86) PCT No.: PCT/JP99/02261

§ 371 (c)(1), (2), (4) Date: Jan. 12, 2001

(87) PCT Pub. No.: WO99/58536

PCT Pub. Date: Nov. 18, 1999

(30) Foreign Application Priority Data

May 8, 1998 (JP) ............................................. 10-142151

(51) Int. Cl.[7] .................. C07D 519/06; A61K 31/437; A61K 31/519; A61K 31/55; A61P 31/04
(52) U.S. Cl. .................................. 514/210.12; 540/350
(58) Field of Search ....................... 540/350; 514/210.12

(56) References Cited

U.S. PATENT DOCUMENTS

| | | |
|---|---|---|
| 4,840,946 A | 6/1989 | Habich et al. |
| 5,104,867 A | 4/1992 | Kawamoto et al. |
| 5,496,816 A | 3/1996 | Blizzard et al. |

FOREIGN PATENT DOCUMENTS

| | | |
|---|---|---|
| JP | 63-145280 | 6/1988 |
| JP | 2223587 A | 7/1989 |
| JP | 228180 | 1/1990 |
| JP | 223587 | 9/1990 |
| WO | 9525108 | 9/1995 |

OTHER PUBLICATIONS

Shinagawa et al., *Bioorganic and Medicinal Chemistry*, 5(3): 601–621 (1997).

*Primary Examiner*—Mark L. Berch
(74) *Attorney, Agent, or Firm*—Birch, Stewart, Kolasch & Birch, LLP

(57) ABSTRACT

Novel β-lactam compound of the formula [1]:

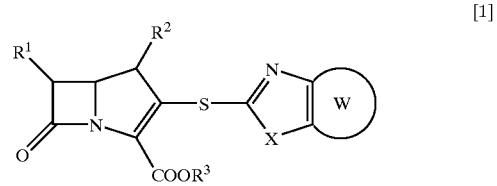

wherein $R^1$ is lower alkyl or hydroxy-substituted lower alkyl, $R^2$ is H or lower alkyl, X is O or, S, $R^3$ is H, metal or protecting group, W is a 6- or 7-membered nitrogen-containing heterocycle optionally being substituted at carbon atoms. Said β-lactam compound shows excellent antibacterial activity against Gram-positive bacteria, particularly against methicillin-resistant *Staphylococcus aureus* and methicillin-resistant and coagulase-negative *Staphylococcus aureus*.

10 Claims, No Drawings

β-LACTAM COMPOUNDS AND PROCESS FOR PRODUCING THE SAME

This application is the national phase under 35 U.S.C. §371 of PCT International Application No. PCT/JP99/02261 which has an International filing date of Apr. 28, 1999, which designated the United States of America.

TECHNICAL FIELD

The present invention relates to a novel β-lactam compound represented by the formula [1] as described below.

BACKGROUND ART

By the wide clinical application of the third-generation cephalosporins, Gram-positive bacteria have become to be frequently isolated. Particularly, methicillin-resistant *Staphylococcus aureus* (hereinafter, referred to as MRSA) has been more frequently isolated, and becomes a serious problem in clinical field, because infectious diseases caused by MRSA are difficult to be treated. Although vancomycin has been broadly used for infectious diseases caused by MRSA in these days, it has a defect in difficulty of administration because of its side effects, and further glycopeptide-resistant bacteria are supposed to increase in future by administration thereof. Moreover, it has recently been reported the increase in isolation of methicillin-resistant and coagulase-negative Staphylococci (MRCNS). Under these circumstances, it has been desired to develop a safe medicament having potent anti-MRSA and anti-MRCNS activities.

DISCLOSURE OF INVENTION

An object of the present invention is to provide a β-lactam antibiotic having an excellent antibacterial activity against Gram-positive bacteria, especially against MRSA and MRCNS.

The present inventors have intensively studied, and have found that a compound of the following formula [1] shows a potent effect on Gram-positive bacteria, and shows an excellent antibacterial activity especially against MRSA and MRCNS, and have accomplished the present invention.

That is, the present invention relates to a β-lactam compound of the following formula [1], a pharmaceutical composition containing the same as an active ingredient, and a process for producing the same.

(1) A β-lactam compound of the formula [1]:

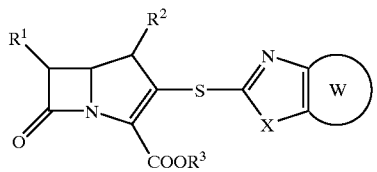

[1]

wherein $R^1$ is a lower alkyl group or a lower alkyl group being substituted by a hydroxy group; $R^2$ is a hydrogen atom or a lower alkyl group; X is an oxygen atom or a sulfur atom; $R^3$ is a hydrogen atom, an anion, a pharmaceutically acceptable metal, or a protecting group for a carboxyl group; Ring W is a 6- or 7-membered heterocyclic group containing 1 to 2 nitrogen atoms and 1 to 3 double bonds, which may optionally contain 1 to 2 carbonyl carbon atoms at any position which is chemically possible, and the carbon atoms of Ring W are not substituted or have the following substituents: a) $R^a$ ($R^a$ is a substituted or unsubstituted lower alkyl group or a substituted or unsubstituted cycloalkyl group), b) A (A is a substituted or unsubstituted aryl group), c) —OH or —OP$^a$ (P$^a$ is a protecting group for a hydroxy group), d) —OR$^a$ (R$^a$ is as defined above), e) —OA (A is as defined above), f) —NH$_2$ or —NHP$^b$ (P$^b$ is a protecting group for an amino group), g) —NHR$^a$, —N(R$^b$)R$^c$ or —N(R$^a$)P$^b$ (R$^a$ and P$^b$ are as defined above, R$^b$ and R$^c$ are a substituted or unsubstituted lower alkyl group or a substituted or unsubstituted cycloalkyl group, or R$^b$ and R$^c$ may combine each other together with the nitrogen atom to which they bond, and form a 3- to 7-membered heterocyclic group having optionally 1 to 2 other heteroatoms selected from an oxygen atom, a sulfur atom and a nitrogen atom, and having optionally a substituent, h) —NHA or —N(A)P$^b$ (A and P$^b$ are as defined above), i) —N(R$^a$)A (A and R$^a$ are as defined above), j) —CONH$_2$, k) —CONHR$^a$, —CON(R$^b$)R$^c$ (R$^a$, R$^b$ and R$^c$ are as defined above), l) —CONHA (A is as defined above), m) —CON(R$^a$)A (A and R$^a$ are as defined above), n) —CONHC(=NH)NH$_2$ or —CONHC(=NP$^b$)NHP$^b$ (P$^b$ is as defined above), o) —COOH or —COOP$^c$ (P$^c$ is a protecting group for a carboxyl group), p) —COOR$^a$ (R$^a$ is as defined above), q) —COOA (A is as defined above), r) —COR$^a$ (R$^a$ is as defined above), s) —COA (A is as defined above), t) a halogen atom. The nitrogen atoms of Ring W are not substituted or have the following substituents: a) $R^a$ ($R^a$ is as defined above), b) —CH=NH or —CH=NP$^b$ (P$^b$ is as defined above), c) —C(R$^a$)=NH or —C(R$^a$)=NP$^b$ (R$^a$ and P$^b$ are as defined above), provided that when the nitrogen atoms of Ring W are not substituted, then the carbon atoms of Ring W are not substituted either, and one nitrogen atom of Ring W may be quaternary one, and when said nitrogen atom has no double bond, then said nitrogen atom may be a quaternary one having 2 substituents mentioned above, or a pharmaceutically acceptable salt thereof, or a non-toxic ester thereof.

(2) The β-lactam compound according to the above (1), wherein X is a sulfur atom, or a pharmaceutically acceptable salt thereof, or a non-toxic ester thereof.

(3) The β-lactam compound according to any one of the above (1) and (2), wherein $R^1$ is a 1-(R)-hydroxyethyl group, or a pharmaceutically acceptable salt thereof, or a non-toxic ester thereof.

(4) The β-lactam compound according to any one of the above (1), (2) and (3), wherein Ring W is a 6-membered ring, or a pharmaceutically acceptable salt thereof, or a non-toxic ester thereof.

(5) The β-lactam compound according to any one of the above (1), (2), (3) and (4), wherein Ring W contains one nitrogen atom, or a pharmaceutically acceptable salt thereof, or a non-toxic ester thereof.

(6) The β-lactam compound according to any one of the above (1), (2), (3), (4) and (5), wherein the carbon atoms of Ring W are not substituted, or a pharmaceutically acceptable salt thereof, or a non-toxic ester thereof.

(7) The β-lactam compound according to any one of the above (1), (2), (3), (4), (5) and (6), wherein the nitrogen atom of Ring W has a substituent as mentioned above, or a pharmaceutically acceptable salt thereof, or a non-toxic ester thereof.

(8) The β-lactam compound according to any one of the above (1), (2), (3), (4), (5), (6) and (7), wherein Ring W is a pyridine ring, and the nitrogen atom thereof is substituted by a $R^a$, or a pharmaceutically acceptable salt thereof, or a non-toxic ester thereof.

(9) A process for producing a β-lactam compound of the formula [1]:

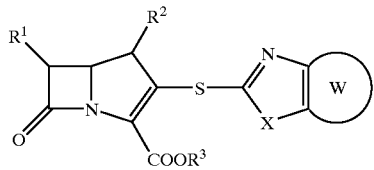

wherein $R^1$, $R^2$, $R^3$, X and Ring W are as defined above, or a pharmaceutically acceptable salt thereof, or a non-toxic ester thereof, which comprises
reacting a compound of the formula [2]:

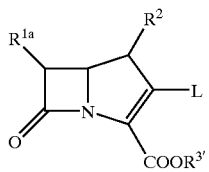

wherein $R^2$ is as defined above, $R^{1a}$ is a lower alkyl group, a lower alkyl group being substituted by a hydroxy group, or a lower alkyl group being substituted by a hydroxy group protected by a protecting group, $R^{3'}$ is a protecting group for a carboxyl group, and L is an active ester of hydroxy group, with a compound of the formula [3]:

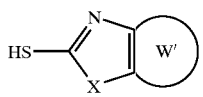

wherein X is as defined above, Ring W' is a 6- or 7-membered heterocyclic group containing 1 to 2 nitrogen atoms and 1 to 3 double bonds, which may optionally contain 1 to 2 carbonyl carbon atoms at any position which is chemically possible, and the carbon atoms of Ring W' are not substituted or substituted by the above-mentioned substituents, and the nitrogen atoms of Ring W' are not substituted or substituted by the following substituents: a) $R^a$ ($R^a$ is as defined above), b) —CH=NH or —CH=$NP^b$ ($P^b$ is as defined above), c) —C($R^a$)=NH or —C($R^a$)=$NP^b$ ($R^a$ and $R^b$ are as defined above), d) $P^b$ ($P^b$ is as defined above), provided that when the nitrogen atoms of Ring W' are not substituted, then the carbon atoms of Ring W' are not substituted either,
in the presence of a base, or reacting the compound of the formula [2] with a salt of the compound [3] with a base (hereinafter, simply referred to as a thiolate) to give a compound of the formula [4]:

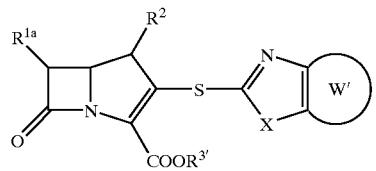

wherein $R^{1a}$, $R^2$, $R^{3'}$, X and Ring W' are as defined above, followed by an appropriate combination of reactions which are properly selected from the removal of the protecting group for hydroxy group for $R^{1a}$, the removal of each protecting group for Ring W', the subsequent alkylation reaction or the imidoylization reaction of the nitrogen atoms of Ring W', and the removal of the protecting group $R^{3'}$ for carboxyl group.

(10) A medicament containing the β-lactam compound as set forth in any one of the above (1), (2), (3), (4), (5), (6), (7) and (8), or a pharmaceutically acceptable salt thereof, or a non-toxic ester thereof.

(11) An antibacterial agent containing the β-lactam compound as set forth in any one of the above (1), (2), (3), (4), (5), (6), (7) and (8), or a pharmaceutically acceptable salt thereof, or a non-toxic ester thereof.

The lower alkyl group for $R^1$, $R^{1a}$ or $R^2$ in the above formulae [1], [2] and [4] includes a straight chain or branched chain alkyl group having 1 to 5 carbon atoms, for example, methyl, ethyl, n-propyl, isopropyl, n-butyl, isobutyl, tert-butyl, and n-pentyl.

The lower alkyl group being substituted by a hydroxy group for $R^1$ or $R^{1a}$ includes ones wherein the alkyl moiety has 1 to 5 carbon atoms, for example, hydroxymethyl, 1-hydroxyethyl, 2-hydroxyethyl, 1-hydroxy-1-methylethyl, 1-hydroxypropyl, and 2-hydroxypropyl.

Ring W and Ring W' may be a 6- or 7-membered nitrogen-containing heterocyclic group such as pyridine, pyrazine, pyridazine, pyrimidine, azepine, diazepine, or a dihydro form or a tetrahydro form of these rings.

The lower alkyl group for the substituents $R^a$, $R^b$ and $R^c$ of Ring W and Ring W' includes a straight chain or branched chain alkyl group having 1 to 5 carbon atoms, for example, methyl, ethyl, n-propyl, n-butyl, isopropyl, isobutyl, etc., and the cycloalkyl group includes a cycloalkyl group having 3 to 6 carbon atoms, for example, cyclopropyl, cyclopentyl, cyclohexyl, etc.

The substituent of the substituted lower alkyl group and the substituted cycloalkyl group for $R^a$, $R^b$ and $R^c$ includes, for example, an aryl group; a substituted aryl group; a hydroxy group; a lower alkoxy group; a lower alkoxy group being substituted by a hydroxy group; a lower alkoxy group being substituted by an amino group; a lower alkylcarbonyloxy group; a lower alkoxycarbonyl group; a lower alkylcarbonyl group; an amino group; a mono- or di-(lower alkyl)amino group (said lower alkyl group optionally having a substituent selected from an aminocarbonyl group having optionally a lower alkyl substituent, a hydroxy group, a carboxyl group and a lower alkylcarbonyl group); a guanidino group; a carboxyl group; an aminocarbonyl group; a mono- or di-(lower alkyl)aminocarbonyl group (said lower alkyl group optionally having a substituent selected from an aminocarbonyl group optionally having a lower alkyl substituent, a hydroxy group, a carboxyl group and a lower alkylcarbonyl group); a halogen atom; a cyano group; an alkylamidino group having 1 to 3 carbon atoms; a guanidinocarbonyl group. These substituents may optionally be protected by an appropriate protecting group. The positions of these substituents may be any position that is chemically possible, and the substitution either at one position or at more positions is also available.

The 3- to 7-membered heterocyclic group being formed by combining $R^b$ and $R^c$ of —N($R^b$)$R^c$ together with the nitrogen atom includes, for example, aziridinyl, azetidinyl, pyrrolidinyl, piperidinyl, piperazinyl, homopiperazinyl, imidazolinyl, imidazolidinyl, morpholinyl, thiamorpholinyl, etc. The substituent of said heterocyclic group includes, for example, a lower alkyl group and a substituted lower alkyl group. The substituent of said substituted lower alkyl group includes, for example, an aminocarbonyl group, a hydroxy group, a carboxyl group, and a lower alkyl-carbonyl group, and said substituted lower alkyl group is, for example, an aminocarbonylmethyl group, a lower alkyl-aminocarbonylmethyl group, a 2-hydroxyethyl group, etc.

The aryl group includes a carbocyclic aryl group and a heterocyclic aryl group, for example, groups derived from aromatic hydrocarbons or heterocycles such as benzene, pyridine, pyrimidine, pyrazine, furan, pyrrole, thiophene, imidazole, triazole, tetrazole, oxazole, thiazole, thiadiazole, naphthalene, quinoline, isoquinoline, quinoxaline, benzofuran, indole, benzothiophene, benzimidazole, benzoxazole, benzothiazole, etc.

The substituent of the substituted aryl group includes, for example, a lower alkyl group; an aminocarbonyl-lower alkyl group optionally being substituted by a lower alkyl group; a hydroxy-lower alkyl group; a carboxy-lower alkyl group; a lower alkylcarbonyl-lower alkyl group; a hydroxy group; a lower alkoxy group; an amino group; a mono- or di-(lower alkyl)amino group; a formylamino group; a formimido group; an acetimido group; an aminocarbonyl group; a substituted aminocarbonyl group represented by —CONHR$^a$ or —CON($R^b$)$R^c$ ($R^a$, $R^b$ and $R^c$ are as defined above); a guanidino-carbonyl group; a nitro group; a halogen atom; a cyano group; a carboxyl group; a sulfonamide group; and a 5- to 7-membered saturated heterocyclic or heterocyclic aryl group having one or more nitrogen atoms.

The 5- to 7-membered saturated heterocyclic or heterocyclic aryl group having one or more nitrogen atoms includes, for example, pyrrolidinyl, imidazolidinyl, pyrazolidinyl, piperidyl, piperazinyl, hexahydroazepinyl, hexahydrodiazepinyl, pyrrolyl, imidazolyl, pyrazolyl, pyridyl, pyrazinyl, pyrimidyl, pyridazinyl, azepinyl, diazepinyl, etc. These substituents may optionally be protected by an appropriate protecting group. The positions of these substituents may be any position which is chemically possible, and the substitution either at one position or at more positions is also available.

The protecting group for carboxyl group for $R^3$ in the above formula [1], the protecting group for carboxyl group for $P^c$ of Ring W or Ring W' in the above formulae [1], [3] and [4], and the protecting group for carboxyl group for $R^3$ in the above formulae [1] and [2] may be any conventional protecting groups, for example, a straight chain or branched chain lower alkyl group having 1 to 5 carbon atoms (e.g., methyl, ethyl, isopropyl, tert-butyl, etc.), a halogeno-lower alkyl group having 1 to 5 carbon atoms (e.g., 2-iodoethyl, 2,2,2-trichloroethyl), an alkoxymethyl group having 1 to 5 carbon atoms (e.g., methoxymethyl, ethoxymethyl, isobutoxymethyl), an aliphatic acyloxymethyl group having 1 to 5 carbon atoms (e.g., acetoxymethyl, propionyloxymethyl, butyryloxymethyl, pivaloyloxymethyl), a 1-($C_1$–$C_5$)alkoxycarbonyloxyethyl group (e.g., 1-ethoxycarbonyloxyethyl), a substituted or unsubstituted aralkyl group (e.g., benzyl, p-methoxybenzyl, o-nitrobenzyl, p-nitrobenzyl), a lower alkenyl group having 3 to 7 carbon atoms (e.g., allyl, 3-methylallyl), a benzhydryl group, or a phthalidyl group.

The protecting group for hydroxy group for $P^a$ of Ring W or Ring W' in the formulae [1], [3] and [4], the protecting group for hydroxy group for $R^{1a}$ in the formulae [2] and [4], and the protecting group for amino group for $P^b$ of Ring W or Ring W' may be any conventional ones, and preferably a lower alkoxycarbonyl group having 1 to 5 carbon atoms (e.g., tert-butyloxycarbonyl), a halogenoalkoxycarbonyl group having 1 to 5 carbon atoms (e.g., 2-iodoethyloxycarbonyl, 2,2,2-trichloroethyloxycarbonyl), a substituted or unsubstituted lower alkenyloxycarbonyl group having 3 to 7 carbon atoms (e.g., allyloxycarbonyl), a substituted or unsubstituted aralkyloxycarbonyl group (e.g., benzyloxycarbonyl, p-methoxybenzyloxycarbonyl, o-nitrobenzyloxycarbonyl, p-nitrobenzyloxycarbonyl), or a trialkylsilyl group (e.g., trimethylsilyl, triethylsilyl, tert-butyldimethylsilyl).

The halogen atom is fluorine, chlorine, bromine, or iodine.

The pharmaceutically acceptable salt of the compound of the above formula [1] is a conventional non-toxic salt. Such salts include, as a salt with an intramolecular carboxylic acid, a salt with an inorganic base such as sodium, potassium, calcium, magnesium, ammonium, a salt with an organic base such as triethylammonium, pyridinium, diisopropylammonium, or an intramolecular salt being formed with a cation at the 3-side chain such as a quaternary ammonium ion. As a salt with an intramolecular base, a salt with an inorganic acid such as hydrochloric acid, sulfuric acid, phosphoric acid, or a salt with an organic acid such as formic acid, acetic acid, oxalic acid, methanesulfonic acid, benzenesulfonic acid can be exemplified.

The non-toxic ester of the formula [1] includes a conventional pharmaceutically acceptable ester at the 2-carboxyl group of carbapenem antibacterial agents, and may be esters being able to be easily hydrolyzed in the living body, for example, esters with acetoxymethyl, pivaloyloxymethyl, 1-(ethoxycarbonyloxy)ethyl, and phthalidyl.

The β-lactam compound of the formula [1], or a pharmaceutically acceptable salt thereof, or a non-toxic ester thereof may be in the form of an anhydride thereof, a hydrate thereof, or a solvate thereof.

BEST MODE FOR CARRYING OUT THE INVENTION

The process for producing the present compound is illustrated in more detail below.

The compound of the formula [4]:

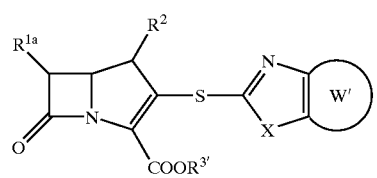

wherein $R^{1a}$, $R^2$, $R^{3'}$, X and Ring W' are as defined above, can be prepared by reacting a compound of the formula [2]:

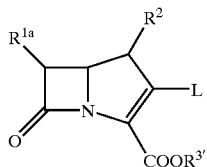

[2]

wherein $R^2$, $R^{1a}$, $R^{3'}$ and L are as defined above, with a compound of the formula [3]:

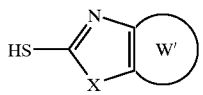

[3]

wherein X and Ring W' are as defined above, in the presence of a base in an inert solvent, or by reacting a compound of the formula [2] with a corresponding thiolate salt of the compound of the formula [3] in an inert solvent.

The active ester of hydroxy group for the substituent L in the above starting compound [2] includes, for example, a substituted or unsubstituted arylsulfonic acid ester (e.g., benzenesulfonic acid ester, p-toluenesulfonic acid ester, p-nitrobenzenesulfonic acid ester, p-bromobenzenesulfonic acid ester, etc.), a lower alkanesulfonic acid ester having 1 to 5 carbon atoms (e.g., methanesulfonic acid ester, ethanesulfonic acid ester, etc.), a halogenoalkanesulfonic acid ester having 1 to 5 carbon atoms (e.g., trifluoromethanesulfonic acid ester, etc.), an arylphosphoric acid ester (e.g., diphenylphosphoric acid ester, etc.), or a halide compound such as chloride, bromide, iodide which is an ester with a hydrogen halide. The preferable reactive ester of hydroxy group may be p-toluenesulfonic acid ester, methanesulfonic acid ester, trifluoromethanesulfonic acid ester, and diphenylphosphoric acid ester.

The inert solvent, which is used in the reaction between the compound [2] and the compound [3] in the presence of a base to give the compound [4], includes, for example, dioxane, tetrahydrofuran, dimethylsulfoxide, dimethylformamide, acetonitrile, benzene, toluene, hexamethylphophoramide, or a mixture of these solvents. The base includes, for example, an inorganic base such as sodium carbonate, potassium carbonate, sodium hydride, potassium hydride, or an organic base such as pyridine, dimethylaminopyridine, triethylamine, diisopropylethylamine, 1,8-diazabicyclo[5.4.0]undec-7-ene (DBU). Especially preferable one is DBU. The base should be used in an amount sufficient for carrying out the reaction, and it is usually used in an amount of 1 to 3 equivalents, to the amount of the mercaptan compound [3].

The mercaptan compound [3] should be used in an amount sufficient for carrying out the reaction, and can be used in a large excess amount, but it is usually used in an amount of 1 to 2 equivalents, to the amount of the compound [2].

The reaction is carried out at a temperature of from −78° C. to +60° C., preferably at a temperature of from −40° C. to +40° C. Besides, after the reaction is completely over, the product thus obtained is isolated by a conventional organic chemical technique.

The inert solvent, which is used in the reaction between the compound [2] and a thiolate salt of the compound [3] to give the compound [4], includes, for example, dioxane, tetrahydrofuran, dimethylsulfoxide, dimethylformamide, acetonitrile, benzene, toluene, hexamethylphosphoramide, or a mixture of these solvents.

In the above reaction, the thiolate salt should be used in an amount sufficient for carrying out the reaction, and can be used in a large excess amount, but it is usually used in an amount of 1 to 2 equivalents, to the amount of the compound [2].

The reaction is carried out at a temperature of from −78° C. to +60° C., more preferably at a temperature of from −40° C. to +40° C. After the reaction is completely over, the product thus obtained is isolated by a conventional organic chemical technique.

The thiolate salt is prepared by reacting the mercaptan compound [3] with a base. The base includes, for example, an inorganic base (e.g., sodium hydride, potassium hydride), a metal alkoxide (e.g., potassium tert-butoxide, sodium methoxide), or a metal amide (e.g., sodium amide, lithium diisopropylamide, lithium disilazide).

The β-lactam compound of the formula [1] is obtained from the compound [4] in a conventional manner by carrying out, optionally combining or simultaneously, reactions such as the removal of the protecting group for hydroxy group for $R^{1a}$, the removal of each protecting group of Ring W', the alkylation reaction or the imidoylization reaction of the nitrogen atoms of Ring W', and the removal of the protecting group for carboxyl group for $R^{3'}$.

The removal of these protecting groups is carried out by treating with an acid, a base, or a reducing agent, and these methods per se are well known methods, as disclosed, for example, in T. W. Greene: Protective Groups in Organic Synthesis, J. Wiley & Sons Inc., 1981. The acid is preferably trifluoroacetic acid, formic acid, boron trifluoride, aluminum chloride, etc., or a mixture of these acids. The base is preferably an alkali metal carbonate (e.g., sodium carbonate, potassium carbonate, etc.), an alkali metal sulfide (e.g., sodium sulfide, potassium sulfide, etc.), or tetrabutylammonium fluoride. The reduction method includes, for example, hydrogenation with zinc and acetic acid, hydrogen and palladium-carbon or platinum, etc. There may be also used palladium (O) compound.

The solvent may be any ones which do not disadvantageously affect the reaction, and includes, for example, water, alcohols (e.g., methanol, ethanol), ethers (e.g., tetrahydrofuran, dioxane), fatty acids (e.g., acetic acid), or a mixture of these solvents. The reaction can possibly be suppressed or promoted by properly lowering or raising the reaction temperature. The preferable reaction temperature is in the range from −30° C. to +40° C. After the reaction is completely over, the product thus obtained can be isolated by a conventional organic chemical technique, for example, by neutralizing the reaction mixture, subjecting it to column chromatography on absorption resin, etc., collecting the fractions containing the desired compound, and then followed by lyophilizing the resultant. The desired compounds can also be obtained by carrying out a combination of the conversion reactions of the groups for Ring W or Ring W' in the formula [4] or [1] before, or after, or simultaneously the removal of the protecting groups. The conversion reactions include, for example, the removal of a protecting group, the imidoylization reaction of an amino group, the quanterization reaction of the nitrogen atoms of Ring W or Ring W', the oxidation reaction or the reduction reaction.

The imidoylization reaction of amino group to obtain the compound [1] from the compound [4] is carried out by subjecting an amino group to substitution reaction with an imidate salt such as benzylformimidate hydrochloride, ethylacetimidate hydrochloride, etc. under weak alkaline conditions. The imidate salt should be used in an amount sufficient for carrying out the reaction, and can be used in a large excess amount, but it is usually used in an amount of 3 to 20 equivalents, to the amount of the compound [4]. The solvent may be any ones which do not disadvantageously affect the reaction, and includes, for example, water, buffers, alcohols (e.g., methanol, ethanol), ethers (e.g., tetrahydrofuran, dioxane), or a mixture of these solvents. The reaction is carried out at a temperature of from −78° C. to +60° C., preferably at a temperature of from −20° C. to +60° C. Besides, after the reaction is completely over, the product thus obtained is isolated by a conventional organic chemical technique.

The alkylation reaction to obtain the compound [1] from the compound [4] is carried out by a substitution reaction with an alkyl halide (e.g., methyl iodide, ethyl iodide) or a substituted alkyl halide (e.g., iodoacetamide, bromoacetone, etc.). The alkyl halide or substituted alkyl halide should be used in an amount sufficient for carrying out the reaction, and can be used in a large excess amount, but it is usually used in an amount of 2 to 20 equivalents, to the amount of the compound [4]. The solvent may be any ones which do not disadvantageously affect the reaction, and preferably ethers (e.g., acetone, tetrahydrofuran, dioxane), or alkyl halides (e.g., methylene chloride, chloroform). The reaction is carried out at a temperature of from −78° C. to +100° C., preferably at a temperature of from −20° C. to +60° C. After the reaction is completely over, the product thus obtained can be isolated by a conventional organic chemical technique.

The compound of the formula [2] is a known compound, and is disclosed, for example, in JP-B-63-55514, EP 0430037 A2, or Tetrahedron Lett., 26, 587 (1985).

The mercaptan compound [3] can be prepared by a combination of conventional various methods, for example, by reacting an α-halo-cyclic carbonyl compound being synthesized by a conventional method with an ammonium dithiocarbamate as shown in the following reaction scheme.

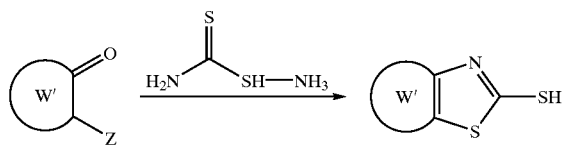

wherein Ring W' is as defined above, and Z is a halogen atom.

When the corresponding starting α-halo-cyclic carbonyl compound cannot be obtained, for example, in case of the synthesis of a compound wherein an aromatic heterocyclic ring and a thiazole ring are fused, the mercaptan compound [3] can be prepared by synthesizing a 1-amino-3-mercapto heterocyclic ring first by a known method, and then treating it with carbon disulfide. As other known method for preparing the mercaptan compound [3], the methods disclosed in literatures such as K. Smith, Chemistry and Industry, May 2, 1988, or Tetrahedron, 21, 1323 (1965), or Monat. Chem., 102, 1010 (1971), or a combination of these are exemplified.

The compound of the above-mentioned formula [1] may have optical isomers based on the asymmetric carbon atoms at the 4-, 5- and 6-positions of the carbapenem nucleus, as shown in the following formula:

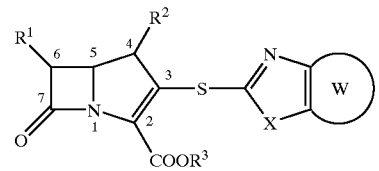

wherein $R^1$, $R^2$, $R^3$, X and Ring W are as defined above, and these isomers are all conveniently expressed by only one formula. However, the scope of the present invention should not be construed to be limited thereby, and includes all isomers and a mixture of isomers based on each asymmetric carbon atom. In addition, the preferable isomers are ones wherein the 5-carbon atom has an R-configuration such as (5R,6R)-compounds or (5R, 6S)-compounds when $R^2$ is a hydrogen atom, and one wherein the 4-carbon atom has an R-configuration and the 5-carbon atom has an S-configuration, such as (4R,5S,6S)-compounds or (4R,5S, 6R)-compounds, when $R^2$ is a lower alkyl group. Moreover, when $R^1$ is 1-hydroxyethyl group, the compound [1] may have isomers having an R-configuration or an S-configuration at the 8-position, as shown in the following formula:

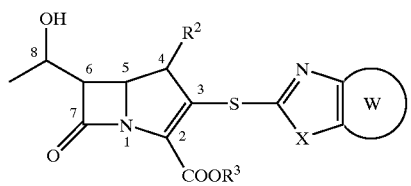

wherein $R^2$, $R^3$, X and Ring W are as defined above, and the preferable one is ones having an R-configuration at the 8-position.

Isomers having such configurations are prepared by using each corresponding isomer of the starting compound [2].

The present compounds of the formula [1] are novel β-lactam compounds having an azolethio group having various substituents at the 3-position of the carbapenem nucleus, and these compounds show an excellent antibacterial activity, and are useful as a medicament.

Representative compounds of the formula [1] obtained by the present invention are exemplified in the following Table 1.

TABLE 1
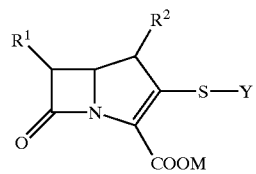
| Compound No. | R¹ | R² | Y |
|---|---|---|---|
| 1 | CH₃CH(OH)— | Me |  |
| 2 | CH₃CH(OH)— | Me |  |
| 3 | CH₃CH(OH)— | Me |  |
| 4 | CH₃CH(OH)— | Me |  |
| 5 | CH₃CH(OH)— | Me |  |
| 6 | CH₃CH(OH)— | Me |  |
| 7 | CH₃CH(OH)— | Me |  |
| 8 | CH₃CH(OH)— | Me |  |
| 9 | CH₃CH(OH)— | Me |  |
| 10 | CH₃CH(OH)— | Me |  |
| 11 | CH₃CH(OH)— | Me |  |

TABLE 1-continued
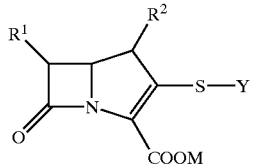
| Compound No. | R¹ | R² | Y |
|---|---|---|---|
| 12 | CH₃CH(OH)— | Me | 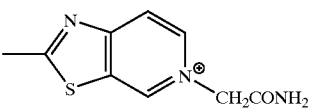 |
| 13 | CH₃CH(OH)— | Me | 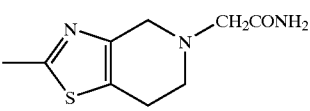 |
| 14 | CH₃CH(OH)— | Me | 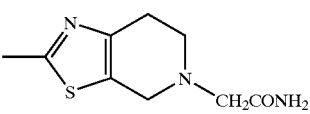 |
| 15 | CH₃CH(OH)— | Me | 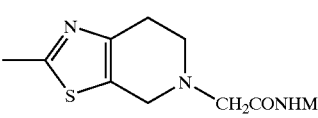 |
| 16 | CH₃CH(OH)— | Me | 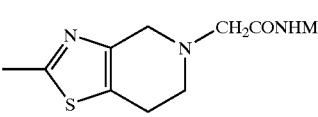 |
| 17 | CH₃CH(OH)— | Me | 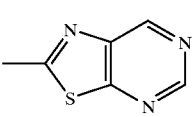 |
| 18 | CH₃CH(OH)— | Me | 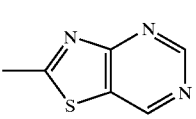 |
| 19 | CH₃CH(OH)— | Me | 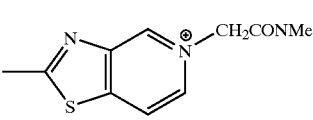 |
| 20 | CH₃CH(OH)— | Me | 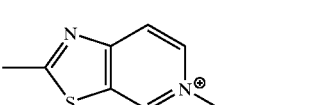 |
| 21 | CH₃CH(OH)— | Me | 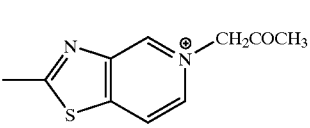 |
| 22 | CH₃CH(OH)— | Me | 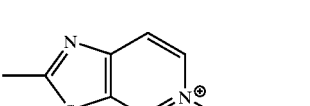 |

TABLE 1-continued

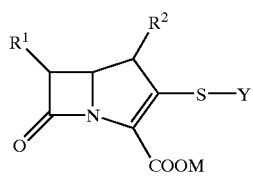

| Compound No. | R¹ | R² | Y |
|---|---|---|---|
| 23 | $CH_3CH(OH)-$ | Me | 2-methyl-thiazolo-pyridinium with $CH_2CONHMe$ (N⁺ at upper position) |
| 24 | $CH_3CH(OH)-$ | Me | 2-methyl-thiazolo-pyridinium with $CH_2CONHMe$ (N⁺ at lower position) |
| 25 | $CH_3CH(OH)-$ | Me | 2-methyl-thiazolo-pyridinium with $CH_2COOH$ (N⁺ at upper position) |
| 26 | $CH_3CH(OH)-$ | Me | 2-methyl-thiazolo-pyridinium with $CH_2COOH$ (N⁺ at lower position) |
| 27 | $CH_3CH(OH)-$ | Me | 2-methyl-4,5,6,7-tetrahydrothiazolo[5,4-b]pyridine (NH at position 4) |
| 28 | $CH_3CH(OH)-$ | Me | 2-methyl-4,5,6,7-tetrahydrothiazolo[5,4-c]pyridine (NH) |
| 29 | $CH_3CH(OH)-$ | Me | 2-methyl-4,5,6,7-tetrahydrothiazolo[4,5-c]pyridine (NH) |
| 30 | $CH_3CH(OH)-$ | Me | 2-methyl-4,5,6,7-tetrahydrothiazolo[4,5-b]pyridine (NH) |
| 31 | $CH_3CH(OH)-$ | Me | 2,4-dimethyl-4,5,6,7-tetrahydrothiazolo[5,4-b]pyridine (N-Me) |
| 32 | $CH_3CH(OH)-$ | Me | 2-methyl-N-methyl-4,5,6,7-tetrahydrothiazolo[5,4-c]pyridine |
| 33 | $CH_3CH(OH)-$ | Me | 2-methyl-N-methyl-4,5,6,7-tetrahydrothiazolo[4,5-c]pyridine |

TABLE 1-continued
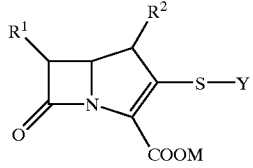
| Compound No. | R¹ | R² | Y |
|---|---|---|---|
| 34 | $CH_3CH(OH)-$ | Me | 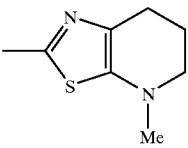 |
| 35 | $CH_3CH(OH)-$ | Me | 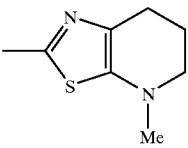 |
| 36 | $CH_3CH(OH)-$ | Me | 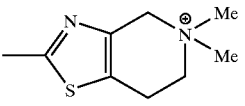 |
| 37 | $CH_3CH(OH)-$ | Me | 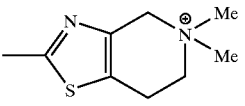 |
| 38 | $CH_3CH(OH)-$ | Me | 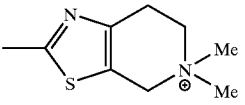 |
| 39 | $CH_3CH(OH)-$ | Me | 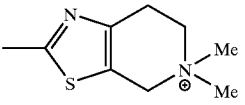 |
| 40 | $CH_3CH(OH)-$ | Me | 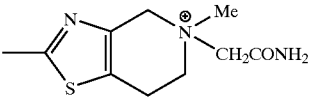 |
| 41 | $CH_3CH(OH)-$ | Me | 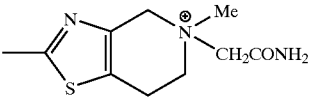 |
| 42 | $CH_3CH(OH)-$ | Me | 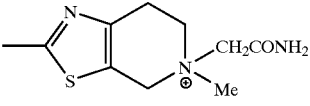 |
| 43 | $CH_3CH(OH)-$ | Me | 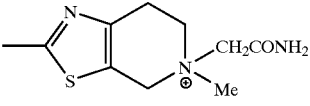 |

TABLE 1-continued
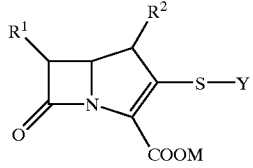
| Compound No. | R¹ | R² | Y |
|---|---|---|---|
| 44 | $CH_3CH(OH)-$ | Me | 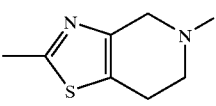 |
| 45 | $CH_3CH(OH)-$ | Me | 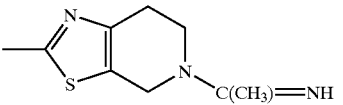 |
| 46 | $CH_3CH(OH)-$ | Me | 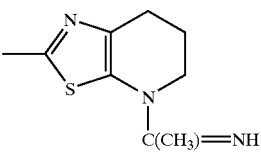 |
| 47 | $CH_3CH(OH)-$ | Me | 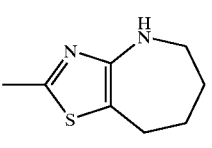 |
| 48 | $CH_3CH(OH)-$ | Me | 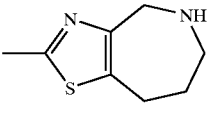 |
| 49 | $CH_3CH(OH)-$ | Me | 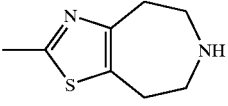 |
| 50 | $CH_3CH(OH)-$ | Me | 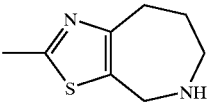 |
| 51 | $CH_3CH(OH)-$ | Me | 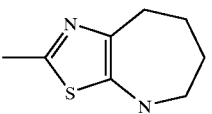 |
| 52 | $CH_3CH(OH)-$ | Me | 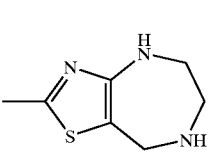 |
| 53 | $CH_3CH(OH)-$ | Me | 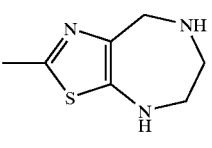 |

TABLE 1-continued

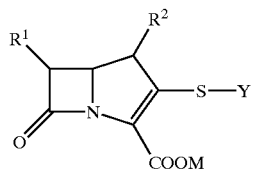

| Compound No. | R¹ | R² | Y |
|---|---|---|---|
| 54 | CH₃CH(OH)— | Me | (2-methyl-thiazolo-diazepine with NH) |
| 55 | CH₃CH(OH)— | Me | (2-methyl-thiazolo-azepine, N-Me) |
| 56 | CH₃CH(OH)— | Me | (2-methyl-thiazolo-azepine, N-Me) |
| 57 | CH₃CH(OH)— | Me | (2-methyl-thiazolo-azepine, N-Me) |
| 58 | CH₃CH(OH)— | Me | (2-methyl-thiazolo-azepine, N-Me) |
| 59 | CH₃CH(OH)— | Me | (2-methyl-thiazolo-azepine, N-Me) |
| 60 | CH₃CH(OH)— | Me | (2-methyl-thiazolo-azepine, N⁺Me₂) |
| 61 | CH₃CH(OH)— | Me | (2-methyl-thiazolo-azepine, N⁺Me-CH₂CONH₂) |
| 62 | CH₃CH(OH)— | Me | (2-methyl-thiazolo-azepine, N⁺Me₂) |

TABLE 1-continued

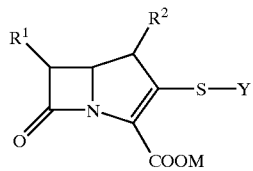

| Compound No. | R[1] | R[2] | Y |
|---|---|---|---|
| 63 | $CH_3CH(OH)-$ | Me | 2-methyl-thiazolo-azepine with N⁺(Me)(CH₂CONH₂) |
| 64 | $CH_3CH(OH)-$ | Me | 2-methyl-thiazolo-azepine with N⁺(Me)₂ |
| 65 | $CH_3CH(OH)-$ | Me | 2-methyl-thiazolo-azepine with N⁺(Me)(CH₂CONH₂) |
| 66 | $CH_3CH(OH)-$ | Me | 2-methyl-thiazolo-azepine with N-CH=NH |
| 67 | $CH_3CH(OH)-$ | Me | 2-methyl-thiazolo-azepine with N-C(CH₃)=NH |
| 68 | $CH_3CH(OH)-$ | Me | 2-methyl-thiazolo-azepine with N-CH=NH |
| 69 | $CH_3CH(OH)-$ | Me | 2-methyl-thiazolo-azepine with N-C(CH₃)=NH |
| 70 | $CH_3CH(OH)-$ | Me | 2-methyl-thiazolo-azepine with N-CH=NH |
| 71 | $CH_3CH(OH)-$ | Me | 2-methyl-thiazolo-azepine with N-C(CH₃)=NH |

TABLE 1-continued

| Compound No. | R¹ | R² | Y |
|---|---|---|---|
| 72 | CH₃CH(OH)— | Me | 4,7-dimethyl-4,5,6,7-tetrahydro-2-methyl-thiazolo-diazepine |
| 73 | CH₃CH(OH)— | Me | 4,7-dimethyl-4,5,6,7-tetrahydro-2-methyl-thiazolo-diazepine (isomer) |
| 74 | CH₃CH(OH)— | Me | 4-methyl-2-methyl-thiazolo-diazepine |
| 75 | CH₃CH(OH)— | Me | 2-methyl-5-oxo-thiazolo-diazepine |
| 76 | HOCH₂— | Me | 2-methyl-N-methyl-thiazolo-pyridinium |
| 77 | HOCH₂— | Me | 2-methyl-N-methyl-thiazolo-pyridinium (isomer) |
| 78 | HOCH₂— | Me | 2-methyl-N-(CH₂CONH₂)-thiazolo-pyridinium |
| 79 | HOCH₂— | Me | 2-methyl-N-(CH₂CONH₂)-thiazolo-pyridinium (isomer) |
| 80 | HOCH₂— | Me | 2-methyl-N,N-dimethyl-thiazolo-pyridinium |

TABLE 1-continued
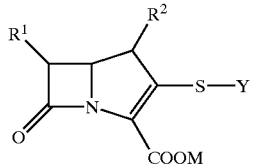
| Compound No. | R¹ | R² | Y |
|---|---|---|---|
| 81 | HOCH$_2$— | Me | 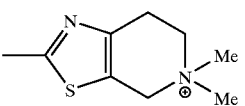 |
| 82 | HOCH$_2$— | Me | 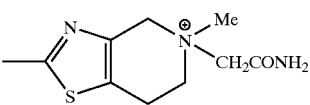 |
| 83 | HOCH$_2$— | Me | 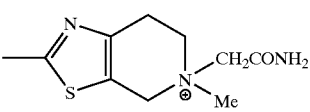 |
| 84 | HOCH$_2$— | Me | 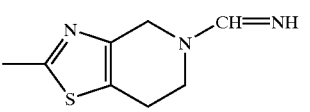 |
| 85 | HOCH$_2$— | Me | 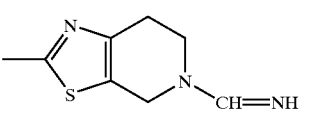 |
| 86 | HOCH$_2$— | Me | 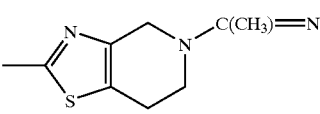 |
| 87 | HOCH$_2$— | Me | 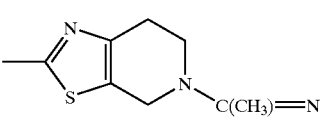 |
| 88 | CH$_3$CH(OH)— | H | 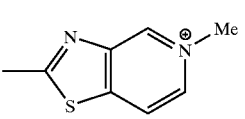 |
| 89 | CH$_3$CH(OH)— | H | 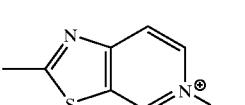 |
| 90 | CH$_3$CH(OH)— | H | 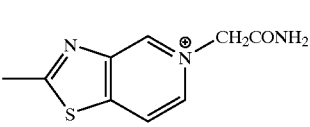 |
| 91 | CH$_3$CH(OH)— | H | 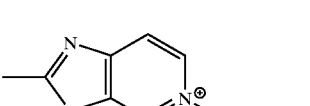 |

TABLE 1-continued
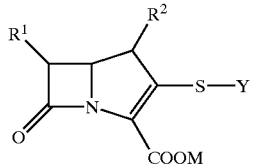
| Compound No. | R¹ | R² | Y |
|---|---|---|---|
| 92 | CH₃CH(OH)— | H | 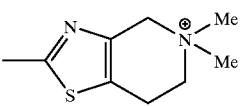 |
| 93 | CH₃CH(OH)— | H | 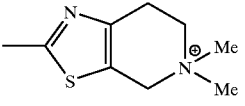 |
| 94 | CH₃CH(OH)— | H | 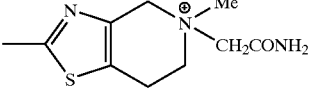 |
| 95 | CH₃CH(OH)— | H | 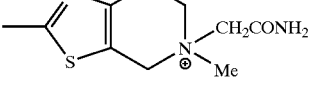 |
| 96 | CH₃CH(OH)— | H | 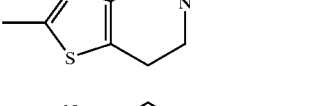 |
| 97 | CH₃CH(OH)— | H | 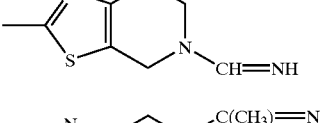 |
| 98 | CH₃CH(OH)— | H | 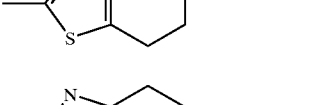 |
| 99 | CH₃CH(OH)— | H | 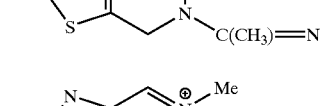 |
| 100 | CH₃CH(OH)— | Me | 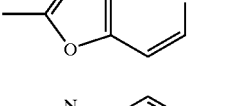 |
| 101 | CH₃CH(OH)— | Me | 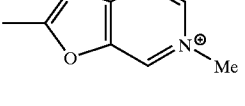 |
| 102 | CH₃CH(OH)— | Me | 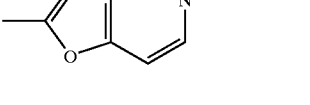 |

TABLE 1-continued

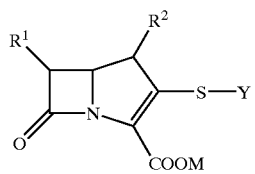

| Compound No. | R¹ | R² | Y |
|---|---|---|---|
| 103 | CH₃CH(OH)— | Me | 2-methyl-oxazolo[5,4-c]pyridinium-CH₂CONH₂ |
| 104 | CH₃CH(OH)— | Me | 2-methyl-4,5,6,7-tetrahydrooxazolo[5,4-c]pyridine-N,N-diMe |
| 105 | CH₃CH(OH)— | Me | 2-methyl-4,5,6,7-tetrahydrooxazolo[5,4-c]pyridine-N,N-diMe (isomer) |
| 106 | CH₃CH(OH)— | Me | 2-methyl-4,5,6,7-tetrahydrooxazolo[5,4-c]pyridine-N-Me,CH₂CONH₂ |
| 107 | CH₃CH(OH)— | Me | 2-methyl-4,5,6,7-tetrahydrooxazolo[5,4-c]pyridine-N-CH₂CONH₂,Me |
| 108 | CH₃CH(OH)— | Me | 2-methyl-4,5,6,7-tetrahydrooxazolo[5,4-c]pyridine-N-CH=NH |
| 109 | CH₃CH(OH)— | Me | 2-methyl-4,5,6,7-tetrahydrooxazolo[5,4-c]pyridine-N-CH=NH (isomer) |
| 110 | CH₃CH(OH)— | Me | 2-methyl-4,5,6,7-tetrahydrooxazolo[5,4-c]pyridine-N-C(CH₃)=NH |
| 111 | CH₃CH(OH)— | Me | 2-methyl-4,5,6,7-tetrahydrooxazolo[5,4-c]pyridine-N-C(CH₃)=NH (isomer) |
| 112 | CH₃CH(OH)— | Me | 2-methyl-4,5,6,7-tetrahydrothiazolo[5,4-c]pyridine-N-CH₂CONMe₂ |
| 113 | CH₃CH(OH)— | Me | 2-methyl-4,5,6,7-tetrahydrothiazolo[5,4-c]pyridine-N-CH₂CONMe₂ (isomer) |

The compounds as listed in Table 1 have stereoisomers as described above, and these exemplified compounds include all of their isomers as well. In addition, when Y in Table 1 contains only a cation, M means an anion, and in all the other cases, M means a hydrogen atom.

The novel β-lactam compounds of the present invention represented by the above formula [1] exhibit antibacterial activities against a wide variety of pathogenic bacteria including Gram-positive bacteria such as *Staphylococcus aureas*, *Staphylococcus epidermidis*, *Streptococcus pyoqenes*, *Streptococcus pneumoniae*, *Enterococcus faecalis*, and Gram-negative bacteria such as *Escherichia coli*, the genus Proteus, *Klebsiella pneumoniae*, *Haemophilus influenzae*, *Neisseria gonorrhoeae*, the genus Branhamella, and especially exhibit excellent antibacterial activities against Gram-positive bacteria, as well as against MRSA and MRCNS.

It is well known that dehydropeptidase-I (DHP-I), a renal enzyme, can easily hydrolyze carbapenem compounds derived from natural resources, but some of the present compounds [1], which are also carbapenem compounds, are stable over DHP-I, and can be used alone, but a DHP-I inhibitor may be used together with the present compound, if necessary.

When used as an antibacterial agent in the treatment of infectious diseases caused by bacteria, the present compounds are administered, for example, orally in the form of a tablet, capsule, powder, syrup, etc., or parenterally such as intravenous injection, intramuscular injection, or intrarectal administration.

The suitable administration forms as mentioned above may be prepared by mixing an active ingredient with a conventional pharmaceutically acceptable carrier, excipient, binder, stabilizer, etc. When administered in the form of an injection, a pharmaceutically acceptable buffering agent, solubilizer, isotonic agent, etc. may be added thereto.

The dosage of the compound [1] varies according to the symptoms, ages, body weights, the administration form, the frequency of the administration, etc., but it is usually in the range of 100 to 3000 mg per day for an adult, which is administered once or divided into several dosage units. Besides, the dosage of the compound [1] may be increased or decreased, if necessary.

The present invention is illustrated in more detail by Examples, but should not be construed to be limited thereto.

The following abbreviations are used in Examples.

PNB: p-Nitrobenzyl group
Me: Methyl group
Tf: Trifluoromethanesulfonyl group
THF: Tetrahydrofuran
DMF: N,N-dimethylformamide

EXAMPLE 1

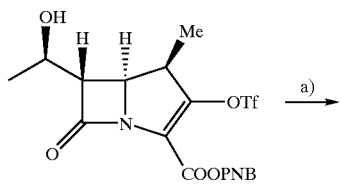

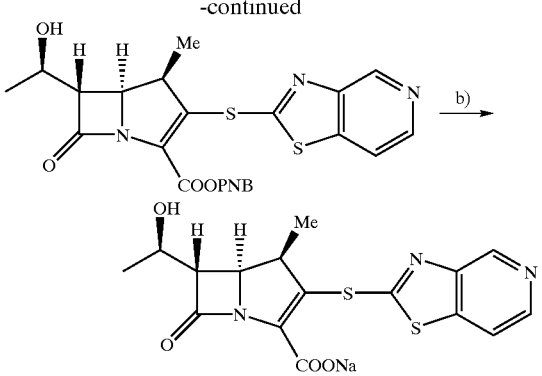

a) A solution of (4R,5R,6S,8R)-p-nitrobenyl-3-trifluoromethanesulfonyloxy-4-methyl-6-(1-hydroxyethyl)-1-azabicyclo[3.2.0]hept-2-en-7-one-2-carboxylate (1.0 g, 2.0 mmol) in dichloromethane (6.0 ml) is stirred at −78° C., and thereto is added dropwise a thiolate solution which is prepared by adding 2-mercapto-pyrido[3,4-d][1,3]thiazole into a suspension of 60% sodium hydride (80 mg, 2.0 mmol) in THF (3.0 ml) and DMF (2.0 m), and the mixture is warmed to 5° C., and allowed to stand at the same temperature for 20 hours. The mixture is diluted with ethyl acetate, washed with water, dried over magnesium sulfate, and the solvent is removed. The resulting oily product is purified by PTLC to give (4R,5R,6S,8R)-p-nitrobenzyl-3-(pyrido[3,4-d][1,3]thiazol-2-ylthio)-4-methyl-6-(1-hydroxyethyl)-1-azabicyclo[3.2.0]hepto-2-en-7-one-2-carboxylate (402 mg, 39%), $^1$H-NMR δ (CDCl$_3$, ppm): 1.17 (3H, d, J=7.3 Hz), 1.33 (3H, d, J=6.3 Hz), 3.38 (1H, dd,J=6.6 and 3.0 Hz), 4.06 (1H,m), 4.30 (1H,m), 4.47 (1H, dd, J=9.2 and 3.0 Hz), 5.31 (1H, d, J=13.9 Hz), 5.62 (1H, d, J=13.9 Hz), 7.65 (2H, d, J=8.9 Hz), 7.77 (1H, d, J=5.3 Hz), 8.22 (2H, d, J=8.9 Hz), 8.53 (1H, d, J=5.3 Hz), 9.23 (1H, s).

b) To a solution of (4R,5R,6S,8R)-p-nitrobenzyl-3-(pyrido[3,4-d][1,3]thiazol-2-ylthio)-4-methyl-6-(1-hydroxyethyl)-1-azabicyclo[3.2.0]hepto-2-en-7-one-2-carboxylate (100 mg, 0.20 mmol) in THF (5.0 ml) and phosphate buffer (pH 7.0, 5.0 ml) is added 10% palladium carbon (100 mg), and the mixture is subjected to hydrogenation at room temperature under atmospheric pressure for 2 hours. The catalyst is removed by filtration, and the filtrate is washed three times with dichloromethane. The organic solvent in the aqueous layer is evaporated under reduced pressure, and the resultant is purified by polymer chromatography (CHP-20P). The fractions eluted with 2–4% aqueous THF solution are combined and lyophilized to give sodium (4R,5R 6S,8R)-3-(pyrido[3,4-d][1,3]thiazol-2-ylthio)-4-methyl-6-(1-hydroxyethyl)-1-azabicyclo[3.2.0]-hepto-2-en-7-one-2-carboxylate as white amorphous.

$^1$H-NMR δ (D$_2$O, ppm): 1.16 (3H, d, J=7.3 Hz), 1.29 (3H, d, J=6.3 Hz), 3.62 (2H, m), 4.29 (1H, m), 4.43 (1H, dd, J=10.3 and 3.3 Hz), 8.05 (1H, d, J=5.6 Hz), 8.43 (1H, d, J=5.6 Hz), 9.04 (1H, s).

EXAMPLE 2

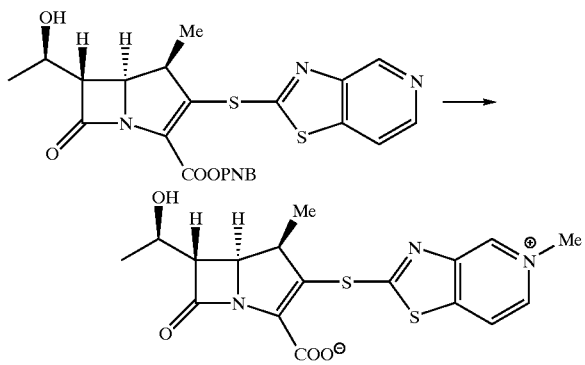

To a solution of (4R,5R,6S,8R)-p-nitrobenzyl-3-(pyrido[3,4-d][1,3]thiazol-2-ylthio)-4-methyl-6-(1-hydroxyethyl)-1-azabicyclo[3.2.0]hepto-2-en-7-one-2-carboxylate (250 mg, 0.49 mmol) in acetone (3.0 ml) is added methyl iodide (1.14 g, 8.0 mmol), and the mixture is allowed to stand at room temperature for one day. The mixture is concentrated under reduced pressure, and the resulting solid is dissolved in a mixture of THF (15 ml) and phosphate buffer (pH 7, 15 ml). To the mixture is added 10% palladium carbon (250 mg), and the mixture is subjected to hydrogenation at room temperature under atmospheric pressure for 2 hours. The catalyst is removed by filtration, and the filtrate is washed three times with dichloromethane. The organic solvent in the aqueous layer is evaporated under reduced pressure, and the resultant is purified by polymer chromatography (CHP-20P). The fractions eluted with 2% aqueous THF solution are combined and lyophilized to give (4R,5R,6S,8R)-3-(5-methylpyrido-[3,4-d][1,3]thiazolio-2-ylthio)-4-methyl-6-(1-hydroxyethyl)-1-azabicyclo[3.2.0]hepto-2-en-7-one-2-carboxylate as white amorphous.

$^1$H-NMR δ ($D_2O$, ppm): 1.21 (3H, d, J=7.3 Hz), 1.31 (3H, d, J=6.3 Hz), 3.70 (2H, m), 4.33 (1H, m), 4.50 (1H, dd, J=9.2 and 3.3 Hz), 4.51 (3H, s), 8.52 (1H, d, J=6.6 Hz), 8.59 (1H, d, J=6.6 Hz), 9.33 (1H,s).

EXAMPLE 3

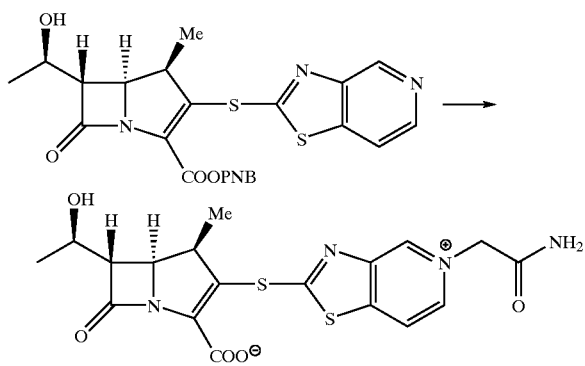

To a solution of (4R,5R,6S,8R)-p-nitrobenzyl-3-(pyrido[3,4-d][1,3]thiazol-2-ylthio)-4-methyl-6-(1-hydroxyethyl)-1-azabicyclo[3.2.0]hepto-2-en-7-one-2-carboxylate (50 mg, 0.098 mmol) in acetone (1.0 ml) is added iodoacetamide (100 mg, 0.54 mmol), and the mixture is allowed to stand at room temperature for one day. The mixture is concentrated under reduced pressure, and thereto is added ethyl acetate, and then the resulting insoluble material is separated by decantation. The resulting material being insoluble in ethyl acetate is dissolved in a mixture of THF (5.0 ml) and phosphate buffer (pH 7.0, 5.0 ml). To the mixture is added 10% palladium carbon (250 mg), and the mixture is subjected to hydrogenation at room temperature under atmospheric pressure for one hour. The catalyst is removed by filtration, and the filtrate is washed three times with dichloromethane. The organic solvent in the aqueous layer is evaporated under reduced pressure, and the resultant is purified by polymer chromatography (CHP-20P). The fractions eluted with 2% aqueous THF solution are combined and lyophilized to give (4R,5R,6S,8R)-3-(5-aminocarbonylmethyl-pyrido[3,4-d][1,3]-thiazolio-2-ylthio)-4-methyl-6-(1-hydroxyethyl)-1-azabicyclo[3.2.0]hepto-2-en-7-one-2-carboxylate as white amorphous.

$^1$H-NMR δ ($D_2O$, ppm): 1.23 (3H, d, J=7.3 Hz), 1.30 (3H, d, J=6.3 Hz), 3.70 (2H, m), 4.30 (1H,m), 4.51 (1H, dd, J=9.2 and 3.3 Hz), 5.60 (2H, s), 8.58 (2H, m), 9.32 (1H, s).

EXAMPLE 4

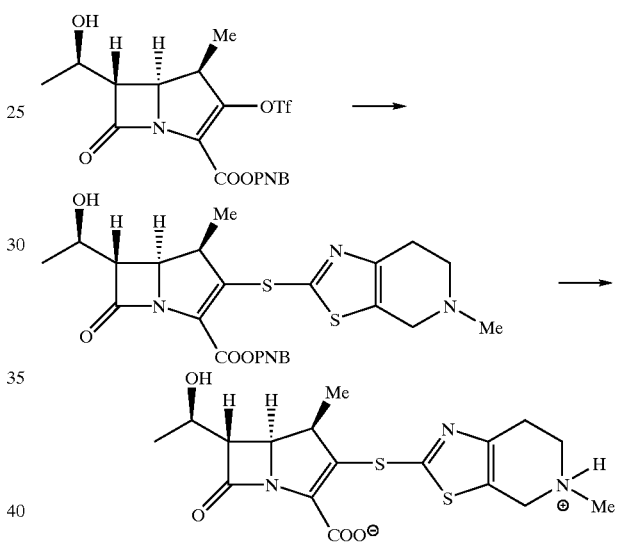

(4R,5R,6S,8R)-3-(6-Methyl-4,5,6,7-tetrahydropyrido-[4,3-d][1,3]thiazolio-2-ylthio)-4-methyl-6-(1-hydroxyethyl)-1-azabicyclo[3.2.0]hepto-2-en-7-one-2-carboxylate is obtained via (4R,5R,6S,8R)-p-nitrobenzyl-3-(6-methyl-4,5,6,7-tetrahydropyrido[3,4-d][1,3]thiazol-2-ylthio)-4-methyl-6-(1-hydroxyethyl)-1-azabicyclo[3.2.0]hepto-2-en-7-one-2-carboxylate in a similar manner as in Example 1 except that 2-mercapto-6-methyl-4,5,6,7-tetrahydropyrido-[4,3-d][1,3]thiazole is used as a thiol.

(4R,5R,6S,8R)-p-nitrobenzyl-3-(6-methyl-4,5,6,7-tetrahydropyrido[4,3-d][1,3]thiazol-2-ylthio)-4-methyl-6-(1-hydroxyethyl)-1-azabicyclo[3.2.0]hepto-2-en-7-one-2-carboxylate, as pale yellow amorphous:

$^1$H-NMR δ ($CDCl_3$, ppm): 1.13 (3H, m), 1.35 (3H, d, J=5.9 Hz), 2.80 (3H×0.5, s), 2.82 (3H×0.5, s), 3.0–3.65 (6H, m), 4.0–4.5 (4H, m), 5.29 (1H, m), 5.53 (1H, d, J=12.9 Hz), 7.67 (2H, d, J=8.3 Hz), 8.24 (2H, d, J=8.3 Hz).

(4R,5R,6S,8R)-3-(6-Methyl-4,5,6,7-tetrahydropyrido-[3,4-d][1,3]thiazolio-2-ylthio)-4-methyl-6-(1-hydroxyethyl)-1-azabicyclo[3.2.0]hepto-2-en-7-one-2-carboxylate, as white amorphous:

$^1$H-NMR δ ($D_2O$, ppm): 1.09 (3H, d, J=7.3 Hz), 1.28 (3H, d, J=6.6 Hz), 2.81 (3H, d, J=5.3 Hz), 3.10 (2H, m), 3.26 (1H, m), 3.42 (2H, m), 3.49 (1H, dd, J=6.3 and 2.5 Hz), 4.20–4.50 (4H, m).

EXAMPLE 5

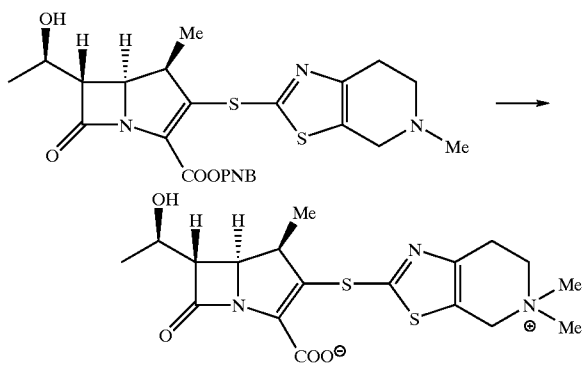

To a solution of (4R,5R,6S,8R)-p-nitrobenzyl-3-(6-methyl-4,5,6,7-tetrahydropyrido[3,4-d][1,3]thiazol-2-ylthio)-4-methyl-6-(1-hydroxyethyl)-1-azabicyclo[3.2.0]hepto-2-en-7-one-2-carboxylate (260 mg, 0.49 mmol) in acetone (3.0 ml) is added methyl iodide (1.14 g, 8.0 mmol), and the mixture is allowed to stand at room temperature for one day. The mixture is concentrated under reduced pressure, and the resulting solid is dissolved in a mixture of THF (15 ml) and phosphate buffer (pH 7, 15 ml). To the mixture is added 10% palladium carbon (260 mg), and the mixture is subjected to hydrogenation at room temperature under atmospheric pressure for 2 hours. The catalyst is removed by filtration, and the filtrate is washed three times with dichloromethane. The organic solvent in the aqueous layer is evaporated under reduced pressure, and the resultant is purified by polymer chromatography (CHP-20P). The fractions eluted with 2% aqueous THF solution are combined and lyophilized to give (4R,5R,6S,8R)-3-(6,6-dimethyl-4,5,6,7-tetrahydropyrido[4,3-d][1,3]thiazolio-2-ylthio)-4-methyl-6-(1-hydroxyethyl)-1-azabicyclo[3.2.0]hepto-2-en-7-one-2-carboxylate.

Examples of a process for preparing the mercapto compound of the formula [3] are explained below. The following abbreviations are used in the following Reference Examples.

t-Boc: tert-butoxycarbonyl group

Bz: Benzoyl group

Reference Example 1

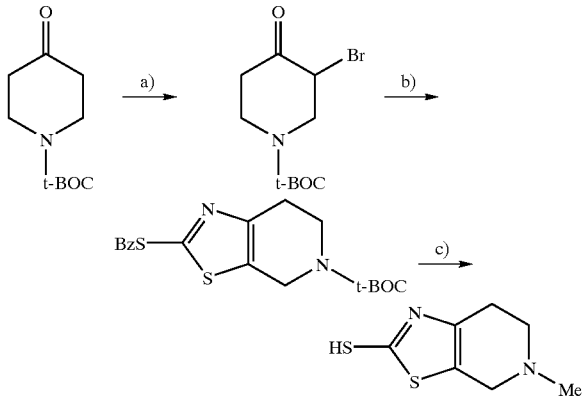

a) N-tert-Butoxycarbonyl-4-piperidone (5.67 g, 28.5 mol) is dissolved in a mixture of dry THF (50 ml) and dry ether (50 ml), and thereto is added anhydrous aluminum chloride (57 mg). To the mixture is gradually added dropwise bromine (1.47 ml, 28.5 mmol) at 0° C., and the mixture is allowed to stand at 5° C. for 24 hours. The resulting reaction solution is diluted with ethyl acetate, and the mixture is washed with a saturated aqueous sodium chloride solution, dried over sodium sulfate, and the solvent is evaporated. The resulting residue is crystallized from ether to give N-tert-butoxycarbonyl-3-bromo-4-piperidone (3.40 g, yield; 43%) as pale yellow crystals.

$^1$H-NMR δ (CDCl$_3$, ppm): 1.51 (9H, s), 2.44 (1H, m), 3.00 (1H, m), 3.5–4.4 (5H, m).

b) N-tert-Butoxycarbonyl-3-bromo-4-piperidone (3.40 g, 12.2 mmol) and ammonium dithiocarbamate (1.48 g, 13.4 mmol) are suspended in ethanol (20 ml), and the mixture is stirred at room temperature for 20 hours. Subsequently, the reaction mixture is warmed to 70° C., and stirred for 1 hour. The reaction mixture is cooled to room temperature, and the solvent is evaporated under reduced pressure. The residue is diluted with methylene chloride, washed with a saturated aqueous sodium chloride solution, dried over sodium sulfate, and concentrated under reduced pressure. The resulting residue is dissolved in dry THF (40 ml), and thereto are added successively triethylamine (2.04 ml, 14.6 mmol) and benzoyl chloride (1.69 ml, 14.6 mmol) under nitrogen atmosphere at 0° C., and the mixture is stirred for 30 minutes under the same conditions. The reaction solution is diluted with ethyl acetate, and washed successively with 1N aqueous hydrochloric acid solution, a saturated aqueous sodium chloride solution, a saturated aqueous sodium hydrogen carbonate solution, and a saturated aqueous sodium chloride solution, and dried over sodium sulfate. The solvent is evaporated under reduced pressure, and the residue is purified by silica gel column chromatography (toluene/ethyl acetate=10) to give 2-benzoylthio-6-(tert-butoxycarbonyl)-4,5,6,7-tetrahydropyrido[4,3-d]-[1,3]thiazole (2.44 g, yield; 53%) as pale yellow amorphous.

$^1$H-NMR δ (CDCl$_3$, ppm): 1.50 (9H, s), 2.95 (2H, m), 3.76 (2H, m), 4.72 (2H, m), 7.52 (2H, m), 7.66 (1H, m), 8.00 (2H, m).

c) To 2-benzoylthio-6-(tert-butoxycarbonyl)-4,5,6,7-tetrahydropyrido[4,3-d][1,3]thiazole (2.44 g, 6.49 mmol) is gradually added dropwise a mixture of anisole (1.41 ml, 12.98 mmol) and trifluoroacetic acid (10.0 ml, 129.8 mmol) at 0° C., and after the addition, the mixture is warmed to room temperature and stirred for 30 minutes. The reaction solution is concentrated under reduced pressure, and to the resulting residue is added methylene chloride. The mixture is concentrated under reduced pressure again, and the resulting residue is crystallized from ether to give pale yellow crystals. The resulting crystals are suspended in THF (30 ml), and thereto is added a 37% aqueous formaldehyde solution (2.04 g, 25.2 mmol) at room temperature, and then further added thereto a 2N aqueous sodium hydroxide solution. The mixture is stirred for one hour, and thereto is added sodium cyanoborohydride (507 mg, 8.06 mmol), and the mixture is further stirred for additional one hour. To the reaction solution is added iN aqueous hydrochloric acid solution to make it weakly acidic, and the mixture is stirred for 30 minutes. The reaction solution is diluted with ethyl acetate, washed with a saturated aqueous sodium hydrogen carbonate solution, dried over sodium sulfate, and concentrated under reduced pressure. The residue is purified by silica gel column chromatography (methylene chloride/methanol=20~10) to give 2-mercapto-6-methyl-4,5,6,7-tetrahydropyrido[4,3-d][1,3]thiazole (525 mg, yield; 44%) as pale yellow amorphous.

$^1$H-NMR δ (CDCl$_3$/CD$_3$OD=10, ppm): 2.79 (2H,m), 2.81 (3H, s), 3.24–3.42 (2H, m), 3.72 (1H, m), 4.06 (1H, d, J=16.2 Hz).

Reference Example 2

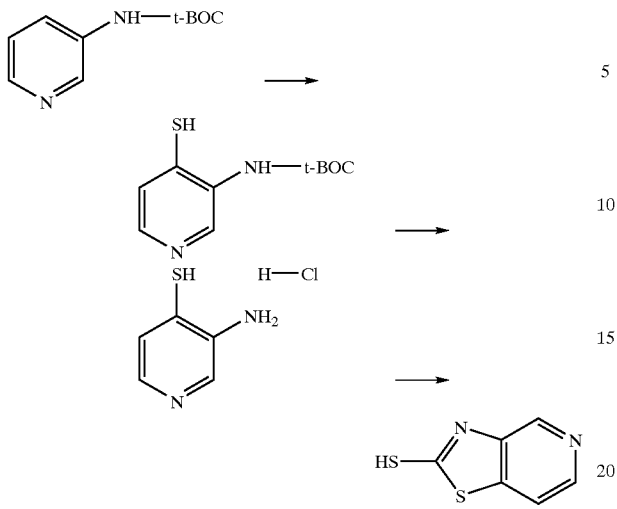

To a solution of 3-t-butyloxycarbonylaminopyridine (5.0 g, 25.6 mmol) in THF (55 ml) is added dropwise n-butyl lithium (1.6 N, 40 ml, 64 mmol) at −78° C. The mixture is warmed to −10° C. 10 minutes thereafter, and then cooled to 78° C. two hours later. To the mixture is added sulfur (1.0 g), and the mixture is warmed to room temperature two hours later. The mixture is stirred for one hour, and thereto is added a saturated aqueous ammonium chloride solution, and extracted with ethyl acetate. The organic layer is washed with water, dried over magnesium sulfate, and concentrated under reduced pressure. The resulting oily product is purified by silica gel column chromatography (benzene/ethyl acetate=2~1) to give 3-t-butyloxycarbonylamino-4-mercaptopyridine (1.68 g, 29%), which is dissolved in acetic acid (35 ml). The resulting solution is added to a 3N solution of hydrogen chloride in acetic acid (15 ml). Four hours thereafter, the mixture is cooled with ice, and the precipitates are collected by filtration, washed with diethyl ether, and dried to give 3-amino-4-mercaptopyridine hydrochloride (906 mg, 75%) as pale yellow crystals. The resulting crystals are treated with carbon disulfide at room temperature in ethanol to give 2-mercaptopyrido[3,4-d][1,3]thiazole as pale yellow crystals. 3-tert-Butyloxycarbonylamino-4-mercaptopyridine:

$^1$H-NMR δ (CDCl$_3$, ppm): 1.51 (9H, s), 7.25 (1H, d, J=6.6 Hz), 7.63 (1H, d, J=6.6 Hz), 8.65 (1H, s), 8.99 (1H, s). 2-Mercaptopyrido[3,4-d][1,3]thiazole:

$^1$H-NMR δ (d$_6$-DMSO, ppm): 7.99 (1H, d, J=5.2 Hz), 8.37 (1H, d, J=5.2 Hz), 8.52 (1H, s).

Industrial Applicability

By the present invention, it becomes possible to provide a β-lactam antibiotic having an excellent antibacterial activity against Gram-positive bacteria, especially against MRSA and MRCNS.

What is claimed is:

1. A β-lactam compound of the formula (1):

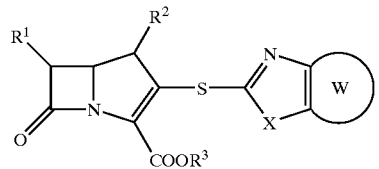

[1]

wherein $R^1$ is a lower alkyl group or a lower alkyl group being substituted by a hydroxy group;

$R^2$ is a hydrogen atom or a lower alkyl group;

X is an oxygen atom or a sulfur atom;

$R^3$ is a hydrogen atom, a pharmaceutically acceptable metal, or a protecting group for. a carboxyl group selected from the group consisting of a straight chain or branched chain lower alkyl group having 1 to 5 carbon atoms, a halogeno-lower alkyl group having 1 to 5 carbon atoms, an alkoxymethyl group having 1 to 5 carbon atoms in the alkoxy moiety, an aliphatic acyloxymethyl group having 1 to 5 carbon atoms in the acyloxy moiety, an aralkyl group, a substituted aralkyl group selected from p-methoxybenzyl, o-nitrobenzyl and p-nitrobenzyl, a lower alkenyl group having 3 to 7 carbon atoms, a benzhydryl group, and a phthalidyl group, or $R^3$ represents an electron when the W ring contains a quaternary nitrogen;

Ring W is a 6- or 7-membered heterocyclic ring made up of carbon atoms and 1 to 2 nitrogen atoms and having 1 to 3 double bonds, the carbon atoms of which ring may optionally include 1 to 2 carbonyl carbon atoms at any position which is chemically possible, and the carbon atoms of Ring W are not substituted, and the nitrogen atoms of Ring W are not substituted or have the following substituents:

a) $R^a$ ($R^a$ is a lower alkyl group or a lower alkyl group substituted by a member selected from (1) an aryl group, (2) a hydroxy group, (3) a lower alkoxy group, (4) a lower alkoxy group being substituted by a hydroxy group, (5) a lower alkoxy group being substituted by an amino group, (6) a lower alkylcarbonyloxy group, (7) a lower alkoxycarbonyl group, (8) a lower alkylcarbonyl group, (9) an amino group, (10) a mono- or di-(lower alkyl)amino group wherein said lower alkyl group optionally has a substituent selected from an aminocarbonyl group having optionally a lower alkyl substituent, a hydroxy group, a carboxyl group and a lower alkylcarbonyl group, (11) a guanidino group, (12) a carboxyl group, (13) an aminocarbonyl group, (14) a mono- or di-(lower alkyl)aminocarbonyl group wherein said lower alkyl group has optionally a substituent selected from an aminocarbonyl group having optionally a lower alkyl substituent, a hydroxy group, a carboxyl group and a lower alkylcarbonyl group, (15) a halogen atom, (16) a cyano group, (17) an alkylamidino group having 1 to 3 carbon atoms, and (18) a guanidinocarbonyl group;

or a cycloalkyl group, or a cycloalkyl group substituted by a member selected from (1) an aryl group, (2) a hydroxy group, (3) a lower alkoxy group, (4) a lower alkoxy group being substituted by a hydroxy group, (5) a lower alkoxy group being substituted by an amino group, (6) a lower alkylcarbonyloxy group, (7) a lower alkoxycarbonyl group, (8) a lower alkylcarbonyl group, (9) an amino group, (10) a mono- or di-(lower alkyl)amino group wherein said lower alkyl group optionally has a substituent selected from an aminocarbonyl group having optionally a lower alkyl substituent, a hydroxy group, a carboxyl group and a lower alkylcarbonyl group, (11) a guanidino group, (12) a carboxyl group, (13) an aminocarbonyl group, (14) a mono- or di-(lower alkyl) aminocarbonyl group wherein said lower alkyl group has optionally a substituent selected from an aminocarbonyl group having optionally a lower alkyl substituent, a hydroxy group, a carboxyl group and a lower alkylcarbonyl group, (15) a halogen atom, (16) a cyano group, (17) an alkylamidino group having 1 to 3 carbon atoms, and (18) a guanidinocarbonyl group;

b) —CH=NH or —CH=NP$^b$ (P$^b$ is a protecting group for an amino group selected from the group consisting of a lower alkoxycarbonyl group having 1 to 5 carbon atoms in the alkoxy moiety, a halogenoalkoxycarbonyl group having 1 to 5 carbon atoms in the alkoxy moiety, a lower alkenyloxycarbonyl group having 3 to 7 carbon atoms, an aralkyloxycarbonyl group, a substituted aralkyloxycarbonyl group selected from p-methoxybenzyloxycarbonyl, o-nitrobenzyloxycarbonyl and p-nitrobenzyloxycarbonyl, and a trialkylsilyl group);

c) —C(R$^a$)=NH or —C(R$^a$)=NP$^b$ (R$^a$ and P$^b$ are as defined above);

provided that when said nitrogen atom of Ring W has a double bond, then said nitrogen atom may be a quaternary one having 1 substituent as mentioned above, and when the nitrogen atom of Ring W has no double bond, then said nitrogen atom may be a quaternary one having 2 substituents as mentioned above;

or a pharmaceutically acceptable salt thereof, or a non-toxic ester thereof.

2. The β-lactam compound according to claim 1, wherein X is a sulfur atom, or a pharmaceutically acceptable salt thereof, or a non-toxic ester thereof.

3. The β-lactam compound according to any one of claims 1 and 2, wherein R$^1$ is a 1-(R)-hydroxyethyl group, or a pharmaceutically acceptable salt thereof, or a non-toxic ester thereof.

4. The β-lactam compound according to any one of claims 1 and 2, wherein Ring W is a 6-membered ring, or a pharmaceutically acceptable salt thereof, or a non-toxic ester thereof.

5. The β-lactam compound according to any one of claims 1 and 2, wherein Ring W contains one nitrogen atom, or a pharmaceutically acceptable salt thereof, or a non-toxic ester thereof.

6. A process for producing a β-lactam compound of the formula (1):

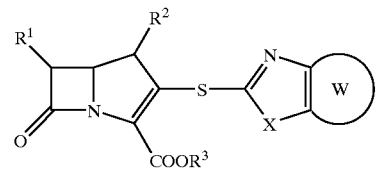

[1]

wherein
R$^1$ is a lower alkyl group or a lower alkyl group being substituted by a hydroxy group;
R$^2$ is a hydrogen atom or a lower alkyl group;
X is an oxygen atom or a sulfur atom;
R$^3$ is a hydrogen atom, a pharmaceutically acceptable metal, or a protecting group for a carboxyl group selected from the group consisting of a straight chain or branched chain lower alkyl group having 1 to 5 carbon atoms, a halogeno-lower alkyl group having 1 to 5 carbon atoms, an alkoxymethyl group having 1 to 5 carbon atoms in the alkoxy moiety, an aliphatic acyloxymethyl group having 1 to 5 carbon atoms in the acyloxy moiety, an aralkyl group, a substituted aralkyl group selected from p-methoxybenzyl, o-nitrobenzyl and p-nitrobenzyl, a lower alkenyl group having 3 to 7 carbon atoms, a benzhydryl group, and a phthalidyl group, or R$^3$ represents an electron when the W ring contains a quaternary nitrogen;
Ring W is a 6- or 7-membered heterocyclic ring made up of carbon atoms and 1 to 2 nitrogen atoms and having 1 to 3 double bonds, the carbon atoms of which ring may optionally include 1 to 2 carbonyl carbon atoms at any position which is chemically possible, and the carbon atoms of Ring W are not substituted, and
the nitrogen atoms of Ring W are not substituted or have the following substituents:
a) R$^a$ (R$^a$ is a lower alkyl group or a lower alkyl group substituted by a member selected from (1) an aryl group, (2) a hydroxy group, (3) a lower alkoxy group, (4) a lower alkoxy group being substituted by a hydroxy group, (5) a lower alkoxy group being substituted by an amino group, (6) a lower alkylcarbonyloxy group, (7) a lower alkoxycarbonyl group, (8) a lower alkylcarbonyl group, (9) an amino group, (10) a mono- or di-(lower alkyl)amino group wherein said lower alkyl group optionally has a substituent selected from an aminocarbonyl group having optionally a lower alkyl substituent, a hydroxy group, a carboxyl group and a lower alkylcarbonyl group, (11) a guanidino group, (12) a carboxyl group, (13) an aminocarbonyl group, (14) a mono- or di-(lower alkyl)aminocarbonyl group wherein said lower alkyl group has optionally a substituent selected from an aminocarbonyl group having optionally a lower alkyl substituent, a hydroxy group, a carboxyl group and a lower alkylcarbonyl group, (15) a halogen atom, (16) a cyano group, (17) an alkylamidino group having 1 to 3 carbon atoms, and (18) a guanidinocarbonyl group; or a cycloalkyl group, or a cycloalkyl group substituted by a member selected from (1) an aryl group, (2) a hydroxy group, (3) a lower alkoxy group, (4) a lower alkoxy group being substituted by a hydroxy group, (5) a lower alkoxy group being substituted by an amino group, (6) a lower alkylcarbonyloxy group, (7) a lower alkoxycarbonyl group, (8) a lower alkylcarbonyl group, (9) an amino group, (10) a mono- or di-(lower alkyl)amino group wherein said lower alkyl group optionally has a substituent selected from an aminocarbonyl group having optionally a lower alkyl substituent, a hydroxy group, a carboxyl group and a lower alkylcarbonyl group, (11) a guanidino group, (12) a carboxyl group, (13) an aminocarbonyl group, (14) a mono- or di-(lower alkyl) aminocarbonyl group wherein said lower alkyl group has optionally a substituent selected from an aminocarbonyl group having optionally a lower alkyl substituent, a hydroxy group, a carboxyl group and a lower alkylcarbonyl group, (15) a halogen atom, (16) a cyano group, (17) an alkylamidino group having 1 to 3 carbon atoms, and (18) a guanidinocarbonyl group;

b) —CH=NH or —CH=NP$^b$ (P$^b$ is a protecting group for an amino group selected from the group consisting of a lower alkoxycarbonyl group having 1 to 5 carbon atoms in the alkoxy moiety, a halogenoalkoxycarbonyl group having 1 to 5 carbon atoms in the alkoxy moiety, a lower alkenyloxycarbonyl group having 3 to 7 carbon atoms, an aralkyloxycarbonyl group, a substituted aralkyloxycarbonyl group selected from p-methoxybenzyloxycarbonyl, o-nitrobenzyloxycarbonyl and p-nitrobenzyloxycarbonyl, and a trialkylsilyl group);

c) —C(R$^a$)=NH or —C(R$^a$)=NP$^b$ (R$^a$ and P$^b$ are as defined above );

provided that when said nitrogen atom of Ring W has a double bond, then said nitrogen atom may be a quaternary one having 1 substituent as mentioned above, and when the nitrogen atom of Ring W has no double bond, then said nitrogen atom may be a quaternary one having 2 substituents as mentioned above;

or a pharmaceutically acceptable salt thereof, or a non-toxic ester thereof, which comprises reacting a compound of the formula (2):

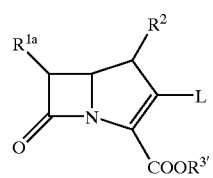

(2)

wherein R$^2$ is as defined above, R$^{1a}$ is a lower alkyl group, a lower alkyl group being substituted by a hydroxy group, or a lower alkyl group being substituted by a hydroxy group protected by a protecting group, R$^{3'}$ is a protecting group for a carboxyl group, and L is an active ester of hydroxy group selected from an arylsulfonic acid ester, a substituted arylsulfonic acid ester selected from p-nitrobenzenesulfonic acid ester and p-bromobenzenesulfonic acid ester, a lower alkanesulfonic acid ester having 1 to 5 carbon atoms, a halogenoalkanesulfonic acid ester having 1 to 5 carbon atoms, and an arylphosphoric acid ester, with a compound of the formula (3):

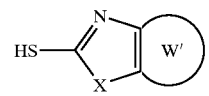

(3)

wherein x is as defined above, Ring W' is a 6- or 7-membered heterocyclic group containing 1 to 2 nitrogen atoms and 1 to 3 double bonds, which may optionally contain 1 to 2 carbonyl carbon atoms at any position which is chemically possible, and the carbon atoms of Ring W' are not substituted, and the nitrogen atoms of Ring W' are not substituted or substituted by the following substituents: a) R$^a$ (R$^a$ is as defined above), b) —CH=NH or —CH=NP$^b$ (P$^b$ is as defined above), c) —C(R$^a$)=NH or —C(R$^a$)=NP$^b$ (R$^a$ and P$^b$ are as defined above), d) P$^b$ (P$^b$ is as defined above), in the presence of a base, or reacting the compound of the formula (2) with a salt of the compound (3) with a base to give a compound of the formula (4):

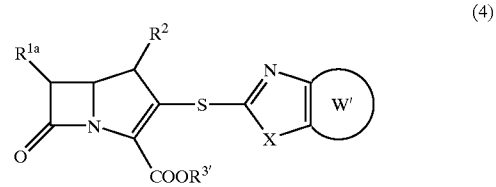

(4)

wherein R$^{1a}$, R$^2$, R$^{3'}$, X and Ring W' are as defined above, followed by an appropriate combination of reactions which are properly selected from the removal of the protecting group for hydroxy group for R$^{1a}$, the removal of each protecting group for hydroxy group, carboxy group and amino group on Ring W', the subsequent alkylation reaction or the imidoylization reaction of the nitrogen atoms of Ring W', and the removal of the protecting group R$^{3'}$ for carboxyl group.

7. The β-lactam compound according to any one of claims 1 and 2, wherein the nitrogen atom of Ring W has a substituent as mentioned in claim 1, or a pharmaceutically acceptable salt thereof, or a non-toxic ester thereof.

8. The β-lactam compound according to any one of claims 1 and 2, wherein Ring W is a pyridine ring, and the nitrogen atom thereof is substituted by a R$^a$, or a pharmaceutically acceptable salt thereof, or a non-toxic ester thereof.

9. A carbapenem compound selected from the compounds as shown by following formulae:

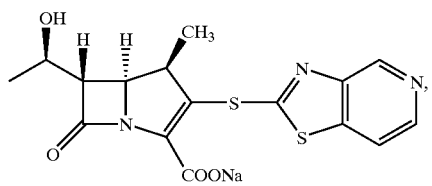

-continued
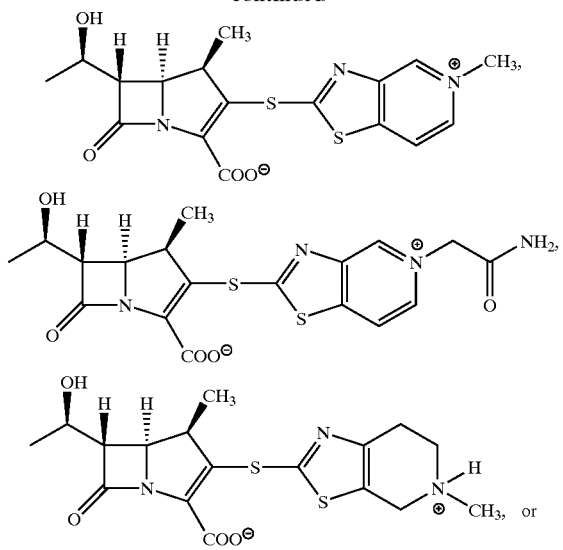
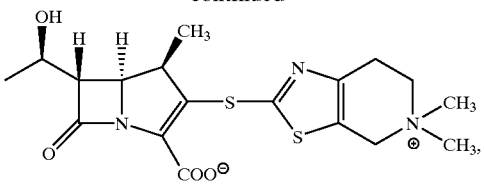
or a pharmaceutically acceptable salt thereof.
10. An antibacterial pharmaceutical composition comprising:
(1) an effective antibacterial amount of the β-lactam compound as set forth in claim 1 or 2, a pharmaceutically acceptable salt thereof, or a non-toxic ester thereof; and
(2) a pharmaceutically acceptable carrier therefor.
* * * * *